United States Patent [19]

Kay

[11] Patent Number: 5,207,652

[45] Date of Patent: May 4, 1993

[54] MEDICAL APPARATUS FIXATION AND INFECTION CONTROL DEVICE

[75] Inventor: Dennis M. Kay, Tampa, Fla.

[73] Assignee: Bioderm, Tampa, Fla.

[21] Appl. No.: 779,729

[22] Filed: Oct. 23, 1991

[51] Int. Cl.$^5$ ............................................. A61M 25/02
[52] U.S. Cl. .............................. 604/180; 128/DIG. 26
[58] Field of Search ................ 604/174, 177, 178, 179, 604/180, 304, 307; 128/DIG. 26

[56] References Cited

U.S. PATENT DOCUMENTS

| | | | |
|---|---|---|---|
| 3,029,188 | 4/1962 | Cyr et al. | 167/60 |
| 3,249,109 | 5/1966 | Maeth et al. | 604/304 |
| 3,339,546 | 9/1967 | Chen | 604/304 |
| 3,683,911 | 8/1972 | McCormick | 604/180 |
| 3,782,377 | 1/1974 | Rychlik | 128/132 |
| 3,900,026 | 8/1975 | Wagner | 128/133 |
| 4,165,748 | 8/1979 | Johnson | 128/348 |
| 4,360,025 | 11/1982 | Edwards | 604/180 |
| 4,367,732 | 1/1983 | Poulsen et al. | 604/307 |
| 4,392,857 | 7/1983 | Beran | 604/179 |
| 4,397,641 | 8/1983 | Jacobs | 604/180 |
| 4,477,325 | 10/1984 | Osburn | 204/159.12 |
| 4,484,914 | 11/1984 | Brown | 604/180 |
| 4,519,793 | 5/1985 | Galindo | 604/180 |
| 4,534,762 | 8/1985 | Heyer | 604/180 |
| 4,645,492 | 2/1987 | Weeks | 604/174 |
| 4,683,882 | 8/1987 | Laird | 604/179 |
| 4,699,616 | 10/1987 | Nowak et al. | 604/180 |
| 4,723,946 | 2/1988 | Kay | 604/267 |
| 4,767,411 | 8/1988 | Edmunds | 604/180 |
| 4,856,504 | 8/1989 | Yamamoto et al. | 604/180 |
| 4,915,694 | 4/1990 | Yamamoto et al. | 604/307 |
| 5,059,189 | 10/1991 | Cilento et al. | 604/307 |

FOREIGN PATENT DOCUMENTS

| | | | |
|---|---|---|---|
| 2451082 | 4/1976 | Fed. Rep. of Germany | 604/180 |
| 148560 | 8/1985 | Japan | 604/174 |

OTHER PUBLICATIONS

Hollister Incorporated, "Hollister Introduces the Horizontal Drain/Tube Attachment Device," *Heart and Lung*, Sep./Oct. 1992, vol. 21, No. 5.

M. C. Johnson Co., Inc., "Cath-Secure Multipurpose Tube Holder" Product Packaging.

Gillespie, et al.; Prevention of Urinary Infection in Gynaecology, pp. 423-425.

Viant, et al.; Improved Method for Preventing Movement of Indwelling Catheters in Female Patients; pp. 736-737.

Kunin, Calvin; Genitourinary Infections in the Patent at Risk; pp. 131-139.

Nickel, et al.; Ultrastructural Study of Microbiologic Colonization of Urinary Catheters.

*Primary Examiner*—Paul J. Hirsch
*Attorney, Agent, or Firm*—Foley & Lardner

[57] ABSTRACT

A device and composition securely affixes an invasive medical apparatus to an entrance site and controls infections associated with the infiltration of microbes along the external walls of such apparatus. Provided in sterile form, the device takes various shapes and sizes and is configured for use with various sizes and types of invasive medical apparatus. The device can incorporate a hydrocolloid composition which, by virtue of is adhesive properties, holds that device in place at a skin entrance site. Alternatively, fixation is effected by adhesive provided on mating surfaces of the device or by thin-film, adhesive leaves. The device achieves a mechanically occlusive seal, a constant presence of medically active substances such as antiseptics and antibiotics at an apparatus skin entrance site, and a substantially rigid attachment of the apparatus to the area around a penetration site which limits the in-and-out motion and accompanying microbial infiltration common in the use of indwelling invasive medical apparatus. The device is particularly useful with catheters, cannulae, drainage devices, and pacemaker wires.

43 Claims, 1 Drawing Sheet

MEDICAL APPARATUS FIXATION AND INFECTION CONTROL DEVICE

BACKGROUND OF THE INVENTION

The present invention relates to an invasive medical apparatus fixation and infection control device for medical and veterinary use and more particularly to a device designed to occlude microorganisms from an apparatus penetration site, effectively limit movement of an invasive medical apparatus at its site of penetration, and to automatically deliver controlled amounts of antiseptic, antibiotic, or other medically active substances to the penetration site.

In many conventional medical procedures, invasive medical apparatus are used to provide access to internal organs, body cavities, and vasculature. Invasive medical apparatus are commonly used to provide routes for the administration of medications or fluids, to provide urinary bladder drainage, to provide for drainage from a fluid filled cavity, to provide ventilation through a tracheostomy site, to provide drainage from pustules and abscesses, to provide monitoring access for measuring renal, cardiac, and other physiological parameters. Invasive medical apparatus commonly penetrate the epidermis by means of existing orifices such as the urethral meatus or nares, and by insertion through the epidermis by puncture or surgically created apertures.

Since invasive medical apparatus entrance sites constitute a breach in the body's epidermal defense barrier, a finite risk of infection exists at a penetration site. The use of catheters and other invasive apparatus is the largest source of infections acquired in hospitals and nursing homes. Such nosocomial, iatrogenic, or induced infections occur much more frequently when invasive medical apparatus are left in place more than a few days. This is so because, after a few days, the pumping or sliding movement of the invasive medical apparatus with respect to the penetration site carries microorganisms through the epidermal barrier to cause infections.

There is a direct relation between the length of time an invasive medical apparatus must remain in place and the likelihood of an infection progressing. One of the reasons for this increase in the incidence of infection is the phenomenon of microbial infiltration along the outside surface of an invasive medical apparatus through the epidermis at the puncture point. This is accomplished by the inexorable deposition and advancement of bacteria within a polysaccharide biofilm in the absence of antiseptic, antibiotic, or antimicrobial substances directly at the skin penetration site.

Various methods and devices for preventing microbial infiltration and the concomitant infection focus upon attempting to immobilize an invasive medical apparatus at its penetration site and/or the application of antiseptic or antibiotic substances to the penetration site. However, before the present invention, there was no method or device which combined the characteristics of the present invention to effectively reduce or eliminate infections associated with the use of invasive medical apparatus.

Conventional surgical tape is commonly used to immobilize an invasive medical apparatus with respect to its penetration site. However, this method simply does not prevent slight in-and-out movements of the invasive medical apparatus with respect to the epidermis caused by patient motion and thus allows exposure of the penetration site to infecting microorganisms. The application of antiseptic or antibiotic substances at the penetration site also has a very limited efficacy with respect to devices before the present invention because there has been heretofore no mechanism for maintaining an effective amount of a medically active substance at the site.

Various means and methods have been developed to approach the problems inherent in invasive medical apparatus and catheter entrance and skin puncture sites. U.S. Pat. No. 3,782,377 to Rychlik discloses the use of a flanged infusion needle puncture site shield having a disinfectant impregnated wick-like member for contacting skin near a puncture site. The shield of Rychlik is made of transparent material for observation of the skin near a puncture site. Rychlik does not, however, effectively immobilize the needle with respect to the entrance site nor does it occlude microorganisms.

U.S. Pat. No. 3,683,911 to McCormick discloses an adhesive backed shield provided with a tubular sleeve defining a passageway for a catheter. The invention of McCormick is also provided with an access slit and adhesive for surrounding a catheter and affixing the shield thereto after the catheter has been inserted into a puncture site. McCormick does not disclose the use of a medically active substance or an effectively occlusive seal against microbial infiltration.

U.S. Pat. No. 4,645,492 to Weeks disclose a device for anchoring catheter tubing to the skin of a patient by means of both adhesive and sutures wherein the in-and-out movement of the catheter is restricted by an arcuate passageway and a locking pawl. Weeks does not disclose the use of a medically active substance nor does it provide an effective seal against microbial infiltration.

U.S. Pat. No. 4,519,793 to Galindo discloses an invasive medical apparatus fixation device particularly adapted for use with ostomy receptacles having a funnel-like tube holding member which is conformable to restrict the movement of a medical tube by frictional means and also having a base provided with an adhesive for attachment to a receptacle surface. Galindo is not adaptable to use with invasive apparatus, however.

U.S. Pat. No. 3,900,026 to Wagner discloses a guard for intravenous needles which comprises a flanged needle entry site housing provided with means for locking a needle to a supply tube and which is adapted to be affixed to a body surface by flanges having adhesive thereon or by supplemental means such as tape. The device of Wagner is transparent for puncture site inspection and is not intended to be use with a medically active substance provided in the chamber formed by the device and the skin while in use. Wagner also lacks means for providing an effective seal against microbial infiltration.

U.S. Pat. No. 4,397,641 to Jacobs discloses a catheter support device for anchoring an intravenous catheter which comprises a rigid annular support member which can be adhesively secured around a puncture site. Jacobs is further provided with means for restraining a portion of the medical tubing leading to a puncture needle thus mechanically isolating disruptive forces transmitted through the catheter from that portion of the catheter tubing which is adjacent to and connected to an infusion needle. Jacobs does not, however, provide any seal whatsoever directly around the puncture site, nor does it contribute a medically active substance to the site.

U.S. Pat. No. 4,767,411 to Edmunds discloses a protective catheter sleeve provided with an open-ended flanged housing wherein the housing is adapted to be adhesively attached to a body surface to form a chamber for receiving and storing antiseptic fluid. Edmunds is also provided with a needle access port in the flanged housing and a slit for the installation and removal of the device from around an indwelling catheter. The housing of Edmunds provides a chamber when in position around an indwelling catheter but does not provide an occlusive seal against microbes nor does it effectively prevent movement of a catheter at its point of epidermal penetration.

The problem of infections associated with invasive medical devices are well recognized. Two examples of publications in the field of urinary infection and sepsis can be found in the work of Gillespie, W.A., Lennon, G.G., Linton, K.B., and Slade, N. "Prevention of Urinary Infection in Gynecology," *British Medical Journal*, August 1964, Volume 2, pages 423-425 ("Gillespie"), and Viant, A.C., Linton, K.B., Gillespie, W.A., Midwinter, A., "Improved Method for Preventing Movement of Indwelling Catheters in Female Patients," *The Lancet*, April, 1971, at pages 736-737 ("Viant").

Thus, it is recognized that immobilizing a catheter securely with respect to its entrance site and providing antiseptic or antimicrobial substances to the entrance site decreases the incidence of infections.

A review of ineffective or attempted solutions to catheter infection and sepsis that depict the state of the art of urinary sepsis and infection, can be found in the work of Kunin, C.M., "Henitourinary Infections in the Patent at Rick: Extrinsic Risk Factors," *The American Journal of Mecicine*, May 15, 1984, at pages 131-138 ("Kunin"). Kunin recognizes that an effective soution for preventing catheter-associated infections and sepsis is not yet available. Bacterial biofilm can provide microorganisms with a certain amount of immunity to antiseptic and/or antimicrobial substances. This has been recognized by Nickel, J. C., Downey, J. A. and Costerton, J. W. in "Ultrastructural Study of Microbiologic colonization of Urinary Catheters," Urology, vol. 34, pg. 284 (1989). Thus, even providing an antiseptic or antimicrobial substance to a medical apparatus penetration site often does not result in an effective zone of aseptic. However, the mechanical occlusion of bacteria from a wound or epidermal opening can prevent bacterial migration via deposition of a biofilm layer. An occlusive wound dressing may prevent the initial formation of a biofilm, layer in close proximity to a wound site or epidermal entry site of an invasive medical apparatus.

Systemic and local penetration site infections from invasive medical apparatus use are believed to result from one of two general causes: (1) intraluminal or intrinsic infections arising from bacteria that migrate internally through the lumen of the invasive medical apparatus to a situs of infection at the internal end of the invasive medical apparatus, and (2) extrinsic infections arise via the migration of bacteria along the external surface of the invasive medical apparatus.

The first means of infection does not apply to the use of solid invasive medical apparatus that do not permit intraluminal transmission. The latter means of infection is thought to be increased by the bacterial secretion of a thin film of mucopolysaccharide material known as "biofilm" along the external surface of an invasive medical apparatus. Bacteria multiplying within a biofilm layer traverse this surface. When such an organic exudate layer exists, the occurrence of infections is further increased by in-and-out motion of the invasive medical apparatus at the site of penetration.

Thus, reduction or elimination of invasive medical apparatus movement is desirable in order to substantially reduce invasive medical apparatus-associated infections. Devices which firmly affix an invasive medical apparatus in relation to its penetration site prevent movement of the invasive medical apparatus into, out of, or in-and-out of the penetration site. Until the present invention, none of the devices available provided effective means to solve the problems associated with invasive medical apparatus.

SUMMARY OF THE INVENTION

It is therefore an object of the present invention to reduce or eliminate microbial infiltration and the resulting infections associated with the use of invasive medical apparatus.

Yet another object of the present invention is to provide a device which can be surroundingly affixed to an indwelling invasive medical apparatus in such a manner that a microbe-impermeable mechanical seal is achieved and movement of the apparatus with respect to its epidermal entrance site is prevented.

It is also an object of the present invention to provide a device which provides medically active substances such as antiseptics or antimicrobials to the epidermal entrance site of an invasive medical apparatus.

It is a similar object of the present invention to provide new hydrocolloid compositions of matter which are inherently adhesive to both invasive medical apparatus and anatomic surfaces.

It is yet a further object of the present invention to provide new hydrocolloid compositions of matter which are releasably comprised of medically active substances.

It is an additional object of the present invention to provide means for protecting the adherent surfaces of the device and for facilitating the sterile transfer thereof to both the invasive medical apparatus and anatomic surfaces.

In accordance with this and other objects of the invention, a fixation and infection control device for use with invasive medical apparatus is provided. The device comprises a barrier body which is impregnated with at least one medically active substance, and has an aperture configured for sealably surrounding the invasive medical apparatus, a first mating surface for joining the barrier body to skin and a second mating surface for joining the barrier body to the invasive medical apparatus. The device is also provided with means for sealably attaching the barrier body to the invasive medical apparatus and the skin so that a microbe-impermeable seal is formed. Preferably, the medically active substance is releasably provided within the barrier body.

In accordance with other objects of the invention, the barrier body is sufficiently rigid and securely attached so that movement of the invasive medical apparatus with respect to the skin and with respect to an entry site of apparatus through the skin is effectively prevented.

The device of the present invention is particularly adapted for use wherein the invasive medical apparatus is indwelling. In one embodiment of the invention, a preferable means for attaching the barrier body is an adhesive disposed on the first and second mating surfaces.

In accordance with other objects of the invention, the device of the present invention can also include additional means for securing the barrier body to the skin. Similarly, the device can further comprise means for additionally securing the barrier body to the invasive medical apparatus. In one embodiment of the invention, the means for additionally securing the barrier body to the apparatus is a closure ring. The closure ring can be provided in the form of a ratcheting ring, a biased O-ring or a spring of a medically acceptable material. In another embodiment of the invention, a flange for additionally securing the barrier body to the invasive medical apparatus is provided.

In accordance with further objects of the invention, the means for additionally affixing the device to skin includes a thin film layer preferably provided as a plurality of adhesive-backed leaves disposed radially about the barrier body. The thin film leaves are provided with release backings for protecting the adhesive until application of the device and for facilitating the sterile transfer of the device to the invasive medical apparatus and the skin.

In accordance with similar objects of the invention, the barrier body is provided with release backings for protecting the mating surfaces and for protecting the means for sealably attaching the barrier body to the invasive medical apparatus and the skin. Preferably, the release backings are substantially U-shaped.

In accordance with additional objects of the invention, the medically active substances provided in the barrier body are one or more antiseptics, antibiotics, pharmaceuticals and/or hormones.

Yet further in accordance with additional objects of the invention, the barrier body is conformable to anatomic shapes. In preferable configurations, the barrier body is elastically conformable to the area surrounding a urethral meatus, the nares or various other anatomical surfaces.

The barrier body of the present invention is preferably formed of a hydrocolloid the composition of which may be varied to control its rigidity, conformability, adhesiveness and its ability to retain and/or release medically active substances. In one preferred embodiment of the device, the hydrocolloid comprises 70% nitrile adhesive, 20% pectin and 10% povidone iodine. In another preferred embodiment, the hydrocolloid comprises 60-80% nitrile adhesive, 10-25% pectin and 10-20% povidone iodine. In yet another embodiment, the barrier body comprises a hydrocolloid of 60% polyisobutylene, 30% pectin and 10% povidone iodine.

In other preferred embodiments of the invention, the barrier body comprises a hydrocolloid of 50-80% polyisobutylene, 20-40% pectin and 5-15% povidone iodine. An alternative preferred formulation is 70% nitrile adhesive, 20% pectin and 10% benzalkonium chloride. Additional preferred embodiments include hydrocolloids of 60% polyisobutylene, 30% pectin and 10% benzalkonium chloride; and those composed of 50-65% polyisobutylene, 25-35% pectin and 1-10% benzalkonium chloride. Another preferred embodiment is a hydrocolloid composed of 70-80% nitrile adhesive, 20-29% pectin and $\frac{1}{2}$-5% benzalkonium chloride.

In accordance with still other objects of the invention, a fixation and infection control device for use with invasive medical apparatus comprising a barrier body formulated of an inherently adhesive compound and having a medically active substance impregnated therein is provided. The device of this preferred embodiment of the present invention has an aperture configured for sealably surrounding an invasive medical apparatus, a first mating surface for joining the barrier body to skin, and a second mating surface for joining the barrier body to the invasive medical apparatus. Preferably, the medically active substance is releasably provided within the barrier body.

In accordance with still further objects of the invention, the first and second mating surfaces are contiguous. Also, the barrier body is sufficiently rigid so that movement of the invasive medical apparatus with respect to the skin and with respect to an entry site of the apparatus through the skin is effectively prevented.

Certain non-hydrocolloid substances are also effective as barrier bodies. A solid wafer of cross-linked polyethylcellulose and polymethylecellulose impregnated with a medically active substance can be utilized for the barrier body of the invention. Wafers of cross-linked polyethylcellulose/polymethylcellulose bioerode when exposed to moisture such as wound exudate or perspiration to release substances impregnated therein. Accordingly, compositions of cross-linked polyethylcellulose/polymethylcellulose impregnated, for example, with povidone iodine, are very suitable for the present invention. Polyethylcellulose/polymethylcellulose wafers are non-adhesive and require a medically acceptable adhesive or hydrocolloid for attachment to skin and to a subject medical apparatus.

Yet other types of barrier bodies are suitable for the invention. For instance, a medically active substance can be enclosed in a pocket created by the sandwiching of a layer of an impermeable film such as polyethylene to a selectively permeable film such as polyurethane. The semipermeable layer of the sandwich is provided with a medically acceptable adhesive which is disposed on skin during use of the invention.

In accordance with additional objects of the present invention, the devices are provided in shapes and configurations particularly suited for use with a wide variety of catheters, cannulae, drainage devices and pacemaker wires.

BRIEF DESCRIPTION OF THE DRAWINGS

So that the invention may be more readily understood, and so that additional features thereof may be appreciated, the invention will now be described by way of example with reference to the accompanying drawings.

DETAILED DESCRIPTION OF THE PREFERRED EMBODIMENTS

Figure 1:
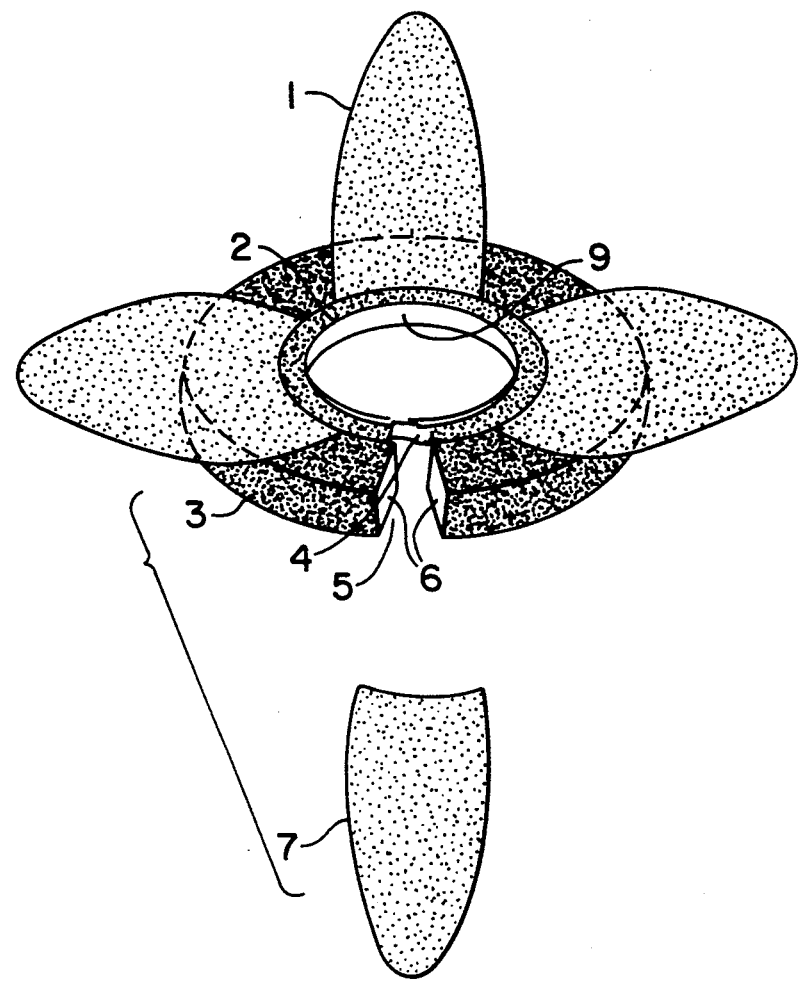
FIG. 1 is a perspective view of a medical apparatus fixation and infection control device of the present invention.

The advantages and characteristics of the fixation and infection control device for use with medical invasive apparatus of the present invention can be elucidated from the following detailed description of one embodiment of the invention to be taken as an example and not as a limitation in conjunction with the accompanying drawings.

From the information disclosed herein, it is also clear that many permutations of the present invention are possible by combining the various components described in the drawings and specification.

With reference to FIG. 1, a fixation and infection control device suitable for use with invasive medical apparatus comprises hydrocolloid ring 3 composed of, for example, 70% synthetic nitrile adhesive (e.g. Vistanex ®, Exxon Corp), 20% pectin (e.g. Benecel ®, Hercules Chemical, Inc.) and 10% povidone iodine (Betadine ®, Purdue-Frederick, Inc.). Numerous other formulations of hydrocolloids within the compositional ranges given in the claims and specification are also suitable for the hydrocolloid barrier body of the invention.

The preferable formulations disclosed are antimicrobial or antiseptic in nature, inherently adhesive to skin and synthetic materials, flexible enough to be spread apart to be surroundingly affixed to an indwelling invasive medical apparatus such as a catheter, and capable of being sealably closed to form a microbe-impermeable seal while being sufficiently rigid to effectively immobilize the catheter or other invasive medical apparatus at its point of entrance into the body. The barrier body is securely attached to the subject medical apparatus and the skin surrounding the apparatus entry site so that device of the present invention effectively prevents unwanted movement of an indwelling medical apparatus. An "indwelling" medical apparatus is one which is already positioned in its desired location penetrating the epidermis.

The term "sufficiently rigid" means that the composition of the barrier body is stiff enough that forces applied to the invasive medical apparatus or to the barrier body which would tend to cause in-and-out "pumping action" motion of the apparatus with respect to the skin entry site or orifice are resisted to the extent that such motion is effectively prevented, thereby eliminating microbial infiltration.

The barrier bodies of the present invention may be formed by die cutting from a flat sheet of the hydrocolloid material, formed releasably in molds, or injection molded into containers which are specifically shaped to retain the fixation and infection control features of the invention.

Within the meaning of the invention, the term "effectively prevents" means that movement of the invasive medical apparatus with respect to the puncture site or orifice at which the apparatus enters the body ("entrance sites") is reduced to such an extent that the apparatus cannot move further into or further out of the body. Thus, the in-and-out "pumping action" motion of the apparatus with respect to the entrance site is so severely limited by the rigidity of the barrier body and its secure attachment to both the invasive apparatus and the skin surrounding the entrance site that microbial infiltration caused by such motion is "effectively prevented."

Barrier body 3 is provided with slit 5 for surroundingly mounting the device around the indwelling medical apparatus and with barrier body mating surfaces for closably forming a mechanical seal about the apparatus. Barrier body 3 is further provided with closure ring 2 for additionally securing the barrier body to the invasive medical apparatus. Closure ring 2 is provided with closure mechanism 4 (shown partially closed in the drawings) which can be opened to permit the device to surround the indwelling apparatus. Closure ring 2 is further provided with mating surface 9 disposed for adherent contact with the medical apparatus. Mating surface 9 is provided with a medically acceptable adhesive or hydrocolloid (not shown) for further affixing the device to a medical apparatus.

The device of the present invention is further provided with adhesive leaves 1 and 7 which may be attached both to closure ring 2 and barrier body 3 for providing additional means of attaching the device to skin. Leaves 1 and 7 are provided with a medically acceptable adhesive (not shown) and U-shaped release backings (not shown) for protecting the adhesive surfaces of the leaves prior to use of the invention. Barrier body 3 is further provided with a skin mating surface (not shown) which is also provided with substantially U-shaped release backings (not shown) for protecting the adhesive surface of barrier body 3 and mating surface 9.

Figure 2:
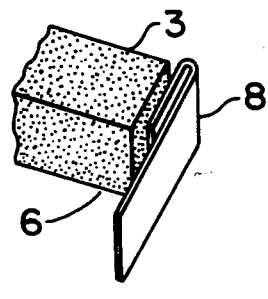
FIG. 2 is a more detailed plan view of the closure elements of the device shown in FIG. 1.

With reference to FIG. 2 a more detailed plan view of the closure elements of the device are shown. Barrier body 3 is provided with closure ring 2 having ratcheting closure mechanism 4 (shown in a partially closed position) disposed for opening and closing at slit 5 when the device is placed around a medical apparatus. Closure ring 2 is further provided with mating surface 9 for sealably contacting and adhering to a medical apparatus.

Figure 3:
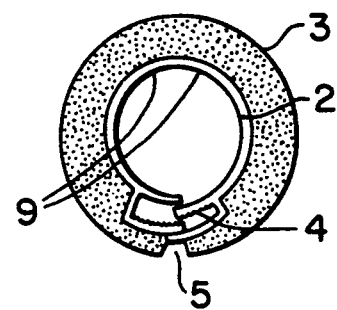
FIG. 3 is an even closer view of a closure surface and release backing assembly of the closure surfaces shown at 5 in FIG. 2.

With reference to FIG. 3, a closer view of a mating surface at slit 5 is shown. Hydrocolloid ring 3 is provided with mating surface 6 which is disposed for intimately contacting an additional mating surface 6 as the device is mounted around a medical apparatus. Mating surface 6 is provided with U-shaped release backing 8 for protecting surface 6 until the device is mounted.

The above described embodiment of the medical apparatus fixation and infection control device operates as described herein below.

The device of the present invention is mounted around an indwelling invasive medical apparatus and applied to a patient's skin using aseptic technique and sterile examination gloves. Closure ring 2 is held open at closure mechanism 4 and slit 5. The device is placed around an indwelling invasive medical apparatus such as a catheter, cannula or wound drain, and is placed firmly about the apparatus at its penetration point on the body so that mating surface 9 and the skin mating surface (not shown) of barrier body 3 are in appropriate position for attachment to the subject apparatus and the skin surface (not shown) surrounding the apparatus skin penetration point, respectively. The release backings (not shown) are removed from the skin mating surface (not shown) of barrier body 3, from closure ring mating surface 9, and from ring slit mating surfaces 6. Closing pressure is applied to barrier body 3 and closure ring 2 so that closure mechanism 4 is engaged and split 5 is sealed by the mating of the adhesives of mating surfaces 6. Thus, mating surface 9 of closure ring 2 is sealably attached to the medical apparatus in a microbe-impermeable manner. "Sealably attached," means that the seal between the barrier body and the apparatus is complete enough to form a microbe-impermeable barrier and to effectively immobilize the barrier body to the apparatus. Similarly, the skin mating surface of barrier body 3 forms a microbe-impermeable seal with the skin around the medical apparatus at the skin penetration site.

Additional affixation force is provided by the application of leaves 1 and 7. After the mating surfaces of closure ring 2 and barrier body 3 are affixed to the apparatus penetration site, release backings are removed from leaves 1 and leaves i are firmly smoothed onto the skin surface. A release backing is also removed from leaf 7 and leaf 7 is applied over barrier body 3 to further seal the juncture of mating surfaces 6 and closure mechanism 4.

The present invention uses a closable ring of hydrocolloid or other material suitable for contributing and/or delivering an antiseptic, antimicrobial or other medically active substance in a controlled manner to the skin surrounding an entrance site of an invasive medical device.

An invasive medical apparatus is any device which enters the body through a natural or artificially created opening on the body surface. Among such devices are included all types of catheters, cannulae and drains, including but not limited to urinary catheters, vascular catheters, peritoneal dialysis catheters, suprapubic catheters, percutaneous enteric catheters, epidural catheters, intraventricular pressure monitors, tracheostomy cannulae, nasal cannulae, wound drainage devices including Jackson-Pratt wound drains, thoracostomy tubes, temporary pacemaker pacing wires, and any other device which breaches a body surface.

The present invention reduces or eliminates the incidence of infection associated with invasive medical device use by providing a zone of aseptic which prevents microbial infiltration around an apparatus entrance site. The zone of aseptic is maintained mechanically by the intimate contact of a barrier body both with the skin surrounding an entrance site and with the invasive apparatus. In one preferred embodiment of the invention, the mechanical seal is achieved by the inherent adhesiveness of the hydrocolloid composition of the barrier body for skin and for the apparatus. In another preferred embodiment, additional means are provided to affix the device in place. More specifically, a closable ring is provided for surroundingly securing the device to the apparatus and adhesive-backed thin film leaves are provided for securing the device to skin.

The barrier body also functions as a microbial-barrier layer, containing an antiseptic agent, for example, povidone iodine or benzalkonium chloride, or an antimicrobial agent to inhibit bacterial growth. The barrier body can also be provided with other medically active substances such as growth hormones or pharmaceuticals which said in healing or in preventing microbial infiltration.

In accordance with the present invention, hydrocolloid compositions other than those conventional in the relevant art are preferred. In preferred embodiments of the present invention, the barrier body layer is a hydrocolloid. One preferred hydrocolloid is composed of a synthetic nitrile adhesive (e.g. Vistanex ®, Exxon Corp) 70%, pectin (e.g. Benecel ®, Hercules Chemical, Inc.) 20% and povidone iodine (Betadine ®, Purdue-Frederick, Inc.) 10%. Another preferred hydrocolloid is composed of 60% polyisobutylene, 30% pectin, and 10% povidone iodine. A similar composition of 60% polyisobutylene, 30% pectin and 10% benzalkonium chloride is also suitable for carrying out the present invention.

In another preferred embodiment, the hydrocolloid constituents are in the ranges of 60-80% nitrile adhesive, 10-25% pectin and 10-20% povidone iodine. Other preferred hydrocolloid constituent ranges are 50-80% polyisobutylene, 20-40% pectin and 5-15% povidone iodine. An alternative preferred formulation range is 50-65% polyisobutylene, 25-35% pectin and 1-10% benzalkonium chloride.

The hydrocolloid barrier body provides several infection control and skin protective functions of the present invention. The barrier body forms an occlusive seal and a mechanical barrier around the invasive medical apparatus entrance site by being placed in intimate contact with both the skin surrounding the site and with the medical apparatus at its point of skin entry. The closure portion of the barrier body is provided such that, in use, it securely and rigidly attaches the barrier body to the invasive medical apparatus. An adhesive or contiguous extension of hydrocolloid on the closure surface which contacts the invasive medical apparatus is provided for this purpose.

Similarly, an adhesive is provided on the skin contacting surface of the barrier body so that the barrier body is also held rigidly and securely in relation to the skin around the invasive medical apparatus penetration site. The hydrocolloid barrier body also functions as an effective moisture barrier and seal. The barrier body is preferably made of a hydrocolloid which absorbs skin perspiration and wound exudate from the invasive medical apparatus skin penetration site thus preventing accumulation of excess moisture and the maceration which often accompanies the accumulation of moisture on a skin surface. In so doing, the barrier body assists in preventing maceration and skin irritation as well as performing the function of preventing microbial infiltration.

To additionally secure long term fixation of the device and invasive medical apparatus, thin-film adhesive leaves are provided as an additional means of attachment. The adhesive coated, vapor permeable thin film leaves are made of a conformable film, enabling the leaves to assume the shape of the underlying skin surface. The leaves are provided with U-shaped release backings which are removed as the device is applied to a skin surface. The U-shaped release backings protect the vapor permeable adhesive prior to application of the device and allow each leaf to be applied to the skin surface in a wrinkle free manor. Preferably, the U-shaped release backings are disposed so that their removal precedes from a line at or near the adhesive leaf's junction with the barrier body in a direction away from the invasive medical apparatus. Each release backing is provided with a pull tab.

With respect to the release backing and pull tab components of the invention, "U-shaped" means the pull tab is substantially parallel to the corresponding release backing and the two are connected at ends by an adhesive or by a weld so that the pull tab and the release backing approximate the arms of the letter "U" with the bottom of the "U" being the connection of the two pieces. This connection is of relatively small dimension when compared to the lengths of the pull tab and backing so that the arms of the "U" are relatively long. Alternatively, a pull tab and release backing can be made of one piece being folded back on itself to also form, substantially, a "U" shape with the fold therein being the bottom of the "U".

The U-shaped release backing preferably is made of a piece of plastic or plastic coated paper which is folded approximately in halves. It has been found that, by using a release backing layer which is almost as flexible as the thin film layer of a different material and having a very low modulus of elongation, wrinkle-free occlusive seals are obtained. One portion of the backing, the release portion, is located over the adhesive on the leaves, such that the adhesive layer is enclosed between the backing and the interior surface of the leaf. The other portion of the backing is folded back away from the leaf and comprises a pull tab. The pull tabs have a sufficiently low modulus of elongation that the application of force to each pull tab in a direction away from the barrier body causes a smooth transverse removal of the backing from the corresponding leaf.

In a preferred embodiment, the release backing portion of the pull tab/release backing assembly has both a very low modulus of elongation and a very high modulus of flexibility. These two characteristics cause the force transmitted when traction is applied to the pull tab portions to be transmitted along a line of separation of the release facing from the thin-film layer such that the thin-film layer remains substantially parallel to the application surface and is applied in a wrinkle-free and occlusive manner. The resulting wrinkle-free layer of film on the skin surface insures the maintenance of the proper location of the device with respect to both the invasive medial apparatus and the underlying skin as well as providing an additional mechanical barrier to moisture and microbial infiltration.

What is claimed is:

1. A fixation and infection control device for use with invasive medical apparatus, comprising
   (a) a flexible barrier body being a pre-determined shape which is impregnated with at least one medically active substance and has
      (i) an aperture configured for sealably surrounding said invasive medical apparatus,
      (ii) a first mating surface for joining said barrier body to skin and
      (iii) a second mating surface for joining said barrier body to said invasive medical apparatus; and
   (b) means for sealably attaching said barrier body to said invasive medical apparatus and said skin so that a microbe-impermeable seal is formed.

2. The device of claim 1, wherein said medically active substance is releasably provided within said barrier body.

3. The device of claim 1, wherein said barrier body is sufficiently rigid so that movement of said invasive medical apparatus with respect to said skin and with respect to an entry site of said apparatus through said skin is effectively prevented.

4. The device of claim 1, wherein said invasive medical apparatus is indwelling.

5. The device of claim 1, wherein said means for attaching said barrier body is an adhesive disposed on said first and second mating surfaces.

6. The device of claim 1, further comprising means (iv) for additionally securing said barrier body to said skin.

7. The device of claim 1, further comprising means (v) for additionally securing said barrier body to said invasive medical apparatus.

8. The device of claim 7 wherein said means (v) comprises a closure ring.

9. The device of claim 8 wherein said means (v) comprises a flange.

10. The device of claim 8 wherein said closure ring comprises a ratchet.

11. The device of claim 6 wherein said means (iv) comprises an adhesive-backed thin film.

12. The device of claim 11 wherein said adhesive-backed thin film comprises a plurality of leaves disposed on said barrier body.

13. The device of claim 12, wherein said thin film leaves are provided with release backings for protecting said adhesive until application of said device and for facilitating the sterile transfer of said device to said invasive medical apparatus and said skin.

14. The device of claim 1, wherein said barrier body is provided with release backings for protecting said mating surfaces and for protecting said means for sealably attaching said barrier body to said invasive medical apparatus and said skin.

15. The device of claim 14, wherein said release backings are substantially U-shaped.

16. The device of claim 1, wherein said medically active substance is an antiseptic.

17. The device of claim 1, wherein said medically active substance is an antibiotic.

18. The device of claim 1, wherein said medically active substance is a pharmaceutical.

19. The device of claim 1, wherein said medically active substance is a hormone.

20. The device of claim 1, wherein said barrier body is conformable to anatomic shapes.

21. The device of claim 1, wherein said barrier body is conformable to the area surrounding a urethral meatus.

22. The device of claim 1, wherein said barrier body comprises a hydrocolloid.

23. The device of claim 22, wherein said hydrocolloid comprises 70% nitrile adhesive, 20% pectin and 10% povidone iodine.

24. The device of claim 22, wherein said hydrocolloid comprises 60–80% nitrile adhesive, 10–25% pectin and 10–20 % povidone iodine.

25. The device of claim 22, wherein said hydrocolloid comprises 60% polyisobutylene, 30%

26. The device of claim 22, wherein said hydrocolloid comprises 50–80% polyisobutylene, 20–40% pectin and 5–15% povidone iodine.

27. The device of claim 22, wherein said hydrocolloid comprises 70% nitrile adhesive, 20% pectin and 10% benzalkonium chloride.

28. The device of claim 22, wherein said hydrocolloid comprises 70–80% nitrile adhesive, 20–29% pectin and ½–5% benzalkonium chloride.

29. The device of claim 22, wherein said hydrocolloid comprises 60% polyisobutylene, 30% pectin and 10% benzalkonium chloride.

30. The device of claim 22, wherein said hydrocolloid comprises 50–65% polyisobutylene, 25–35% pectin and 1–10% benzalkonium chloride.

31. The device of claim 1, wherein said barrier body compresses a wafer of cross-linked polyethylcellulose and polymethylcellulose impregnated with a medically active substance.

32. The device of claim 1, wherein said barrier body comprises any bioerodible polymer compatible with skin and medical applications.

33. The device of claims 4, wherein said fixation and control device is configured to be applicable to and removable from said indwelling catheter without substantial movement of said catheter with respect to said entry site.

34. The device of claim 2, wherein said medically active substance releases from said barrier body at a controlled rate.

35. The device of claim 2, wherein said medically active substance releases from said barrier body at a rate sufficient to deliver said substance to the penetration site of said apparatus and to said mating surfaces in amounts effective to carry out the desired function of said active substance.

36. A fixation and infection control device for use with invasive medical apparatus, comprised of a flexible barrier body being a pre-determined shape comprising an adhesive material, wherein said adhesive material is impregnated with a medically active substance, and having
   (i) an aperture configured for sealably surrounding an invasive medical apparatus,
   (ii) a first mating surface for joining said barrier body to skin, and
   (iii) a second mating surface for joining said barrier body to said invasive medical apparatus.

37. The device of claim 36, wherein said medically active substance is releasably provided within said barrier body.

38. The device of claim 36, wherein said first and second mating surfaces are contiguous.

39. The device of claim 36, wherein said barrier body is sufficiently rigid so that movement of said invasive medical apparatus with respect to said skin and with respect to an entry site of said apparatus through said skin is effectively prevented.

40. The device of claims 1 or 36, wherein said invasive medical apparatus is selected from the group consisting of catheters, cannulae, tracheostomy tubes, drainage devices and pacemaker wires.

41. The device of claim 36, wherein said fixation and control device is configured to be applicable to and removable from said indwelling catheter without substantial movement of said catheter with respect to said entry site.

42. The device of claim 36, wherein said medically active substance releases from said barrier body at a controlled rate.

43. The device of claim 37, wherein said medically active substance releases from said barrier body at a rate sufficient to deliver said substance to the penetration site of said apparatus and to said mating surfaces in amounts effective to carry out the desired function of said active substance.

* * * * *